United States Patent [19]

Mikura et al.

[11] Patent Number: 5,223,515
[45] Date of Patent: Jun. 29, 1993

[54] INJECTABLE SOLUTION CONTAINING A PYRIDYL METHYLSULFINYLBENZIMIDAZOLE

[75] Inventors: Yasushi Mikura, Suita; Akihiro Nagai, Toyono; Hisayoshi Shimizu, Takatsuki, all of Japan

[73] Assignee: Takeda Chemical Industries, Ltd., Osaka, Japan

[21] Appl. No.: 921,996

[22] Filed: Aug. 4, 1992

Related U.S. Application Data

[63] Continuation of Ser. No. 734,129, Jul. 25, 1991, abandoned, which is a continuation of Ser. No. 480,907, Feb. 16, 1990, abandoned, which is a continuation-in-part of Ser. No. 395,357, Aug. 17, 1989, abandoned.

[30] Foreign Application Priority Data

Aug. 18, 1988 [JP] Japan .................. 63-205100

[51] Int. Cl.$^5$ .................. A61K 31/445; A61K 31/13; A61K 31/08
[52] U.S. Cl. .................. 514/322; 514/669; 514/723; 514/925; 546/199
[58] Field of Search ............. 514/338, 925, 322, 723, 514/669; 546/199

[56] References Cited

U.S. PATENT DOCUMENTS

| | | | |
|---|---|---|---|
| 4,337,257 | 6/1982 | Junggren et al. | 514/338 |
| 4,359,465 | 11/1982 | Ruwart | 514/314 |
| 4,472,409 | 9/1984 | Senn-Bilfinger | 514/338 |
| 4,554,280 | 11/1985 | Krasso et al. | 514/338 |
| 4,555,518 | 11/1985 | Rainer | 514/338 |
| 4,689,333 | 8/1987 | Nohara et al. | 514/338 |
| 4,746,667 | 5/1988 | Carlsson et al. | 514/288 |

OTHER PUBLICATIONS

CA105:133883y Nohara et al. Pyridylmethylthio benzimidazdes and their Sulfoxides 1986.
U.S. Merck Index (#5945 & 7644) 9th Edition (1976).
U.S. Pharmacopeiz (1980) pp. 464–465.

*Primary Examiner*—Allen J. Robinson
*Assistant Examiner*—Gary E. Hollinden
*Attorney, Agent, or Firm*—Wegner, Cantor, Mueller & Player

[57] ABSTRACT

An injectable solution of a compound useful as an antiulcer agent of the formula;

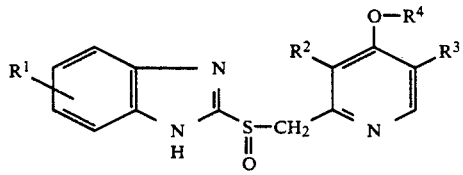

wherein $R^1$ represents hydrogen, methoxy or trifluoromethyl group; $R^2$ and $R^3$, being the same as or different from each other, represent hydrogen or methyl group; and $R^4$ represents a fluorinated $C_2$ to $C_5$ lower alkyl group, is provided by dissolving the compound in at least one of ethanol, propylene glycol and polyethylene glycol; or by dissolving the freeze-dried material of an alkaline aqueous solution of the compound in a mixture of an acidic substance and at least one of the above solvents.

16 Claims, No Drawings

INJECTABLE SOLUTION CONTAINING A PYRIDYL METHYLSULFINYLBENZIMIDAZOLE

This application is a continuation of U.S. application Ser. No. 07/734,129 filed Jul. 25, 1991, now abandoned, which is a continuation of Ser. No. 07/480,907 filed Feb. 16, 1990, abandoned, which is a continuation-in-part of Ser. No. 07/395,357 filed Aug. 17, 1989, abandoned.

This invention relates to injectable solutions containing pyridine derivatives (hereinafter referred to, in some instances, as "Compound (I)") of the below-described formula which are useful as an anti-ulcer agent:

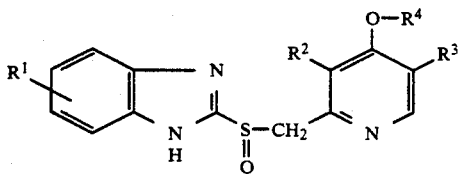

wherein $R^1$ represents hydrogen, methoxy or trifluoromethyl group, $R^2$ and $R^3$, each being the same as, or different from, the other, represent hydrogen or methyl group; and $R^4$ represents fluorinated $C_2$ to $C_5$ lower alkyl group.

There have been known injectable solutions (refer to The European Unexamined Patent Publication No. 124495), which are obtained by dissolving omeprazole sodium having anti-ulcer activity in sterilized water, followed by filtration and lyophilization to give a lyophilized material, which is then dissolved in a sterile-filtered mixed solution of polyethylene glycol 400 for injection, sodium dihydrogenphosphate and sterilized water.

In developing injectable solutions of Compound (I), there are encountered some problems being attributable to its characteristic properties.

Among the species Compound (I), for example, 2-(3-methyl-4-trifluoroethoxy-2-pyridyl)methylsulfinylbenzimidazole (hereinafter referred to briefly as "Compound (I-1)) shows a certain degree of solubility in water but only in the strongly alkaline region of pH 11 or more, with an extremely low solubility in the pH range below pH 11 (33 mg/ml at pH 13, 1 mg/ml at pH 11 and 0.06 to 0.01 mg/ml at pH 9 to 3). Referring to the stability in an aqueous solution, Compound (I-1) is satisfactorily stable in an alkaline solution, but becomes less stable as the pH of the aqueous solution is decreased to the neutral to acidic range, while the resulting solution turns in appearance dark purple in a short period of time.

Thus Compound (I), because of its characteristic properties as described above, has been difficult to process into the dosage form of injectable solution at the physiologically allowable pH range using water alone as a solvent and without employing a sophisticated processing technique, because injectable solutions favorably exhibit a pH value not being far from neutrality in terms of hemolysis, pain or local irritation.

In view of these circumstances described above, the present inventors, after extensive investigation, found that Compound (I) is very soluble in solvents, such as ethanol, propylene glycol and polyethylene glycol, with its stability in said solvents being excellent, and that the powder produced by lyophilizing an alkaline solution of Compound (I) does not tend to discolor with length of time elapsed and is extremely soluble in the above solvents, and the findings, coupled with further research, have culminated into the present invention.

Thus, the present invention is directed to; (1) injectable solutions containing (a) a compound of the formula (I):

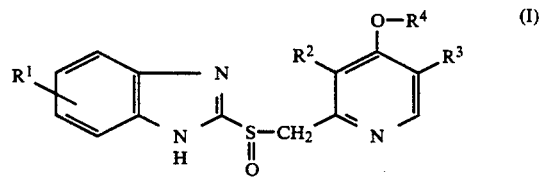

wherein $R^1$ represents hydrogen, methoxy or trifluoromethyl, $R^2$ and $R^3$, each being the same as, or different from, the other, represent hydrogen or methyl; and $R^4$ represents fluorinated $C_2$ to $C_5$ lower alkyl and (b) at least one solvent selected from the group consisting of ethanol, propylene glycol and polyethylene glycol; and (2) Injectable solutions consisting of a lyophilized material of an alkaline solution of Compound (I) being dissolved in a mixed solution composed of (a) an acid substance and (b) at least one solvent selected from the group consisting of ethanol, propylene glycol and polyethylene glycol.

In the above-described formula, examples of the fluorinated $C_2$ to $C_5$ lower alkyl group represented by $R^4$ include 2,2,2-trifluoroethyl, 2,2,3,3,3-pentafluoropropyl, 2,2,3,3-tetrafluoropropyl, 1,1,1-trifluoromethyl, 2,2,2-trifluoroethyl, 2,2,3,3,4,4,4-heptafluorobutyl, 2,2,3,3,4,4,5,5-octafluoropentyl and the like. In the above formula, preferably, $R^1$ and $R^3$ are hydrogen, and $R^2$ is methyl, with $R^4$ being 2,2,2-trifluoroethyl.

It is to be noted that the above-mentioned Compound (I) is a known compound as described in The European Unexamined Patent Publication No. 174726.

As the said polyethylene glycol, there can be used polyethylene glycols having varied average molecular weights, and favorably usable are those having preferably an average molecular weight of 100 to 600.

In the present invention, in cases where ethanol, propylene glycol and polyethylene glycol are used as an admixture of more than two kinds, their mutual mixing ratio may be in any proportions.

When water is contained in the solvent, an increased proportion of water in the total volume of solvent results in a lowered solubility of Compound (I); particularly in the case of Compound (I) being dissolved in the solvent composed of ethanol and water, the dissolved Compound (I) in some instances separates out with lapse of time, and consequently, the proportion of water in the total volume of solvent is desirably not more than 80 % (V/V).

The injectable solutions according to the present invention can be obtained by dissolving Compound (I) in the form of amorphous powder or crystalline powder in the above-mentioned solvent, but it is preferable to dissolve a lyophilized material of an alkaline aqueous solution of Compound (I) in a mixed solution composed of an acidic and the above-mentioned solvent.

As the alkaline aqueous solution of Compound (I), there may be mentioned, for example, an aqueous solution produced by dissolving in water Compound (I) in conjunction with a strongly basic substance such as sodium hydroxide, potassium hydroxide, sodium carbonate, arginine and N-methylglucamine, and adjusting the resulting solution to a pH of not less than 11, preferably not less than 12.

Among the strong basic substances, sodium hydroxide is particularly preferred.

The concentration of Compound (I) in the said alkaline aqueous solution may be of any concentration only if it permits lyophilization, and is preferably 2 to 30 mg/ml, more preferably 5 to 30 mg/ml.

In order to provide the resulting lyophilized material with improved solid-forming property, it is preferred to add to the alkaline aqueous solution sucrose, lactose, neutral amino acids, such as glycine, alanine, proline, valine and methionine, inorganic salts, such as sodium succinate, and the like, These additives can be employed usually in an amount of 0.2 to 5 mg, preferably 0.5 to 3 mg, per mg of Compound (I).

Among these solid-forming agents, mannitol and glycine are preferable, with mannitol being particularly preferred.

The said lyophilized material can be produced by lyophilizing the alkaline aqueous solution of Compound (I) by use of a method known per se, and in general, lyophilization is preferably carried out by means of a method which comprises freezing the solution at a temperature of below −25° C. and drying the frozen material on plates in a dryer by warming the plates up to 25° C. or 40° C. at a rate of 5° to 20° C./hr while keeping the degree of vacuum in the dryer at not more than about 0.1 Torr.

The lyophilized material obtained in this manner produces the appearance of white lump form or powder form, and hardly varies in appearance with length of time elapsed, thereby offering the advantageous characteristic that Compound (I) can be preserved stable for a prolonged period of time.

The said lyophilized material contains a strongly basic substance which has been incorporated therein, therefore, when dissolved in the abovementioned solvent, the material produces a solution with a strong alkalinity. In order to adjust the pH of the solution to a physiologically allowable range, it is preferable to incorporate into the above-mentioned solvent a specifically determined amount of an acidic substance as a pH adjusting agent. Examples of the acidic substance include inorganic acids, such as hydrochloric acid and phosphoric acid, and organic acids, such as sccinic acid and tartaric acid, as well as sodium dihydrogenphosphate, glycine, etc. Among others, hydrochloric acid or sodium dihydrogenphosphate is preferable.

Incidentally, when the pH of the solvent is stabilized by utilizing the buffer capacity of the acidic substance, it is preferable to adjust the pH to desired range by adding a suitable amount of sodium hydroxide etc. thereto, if necessary.

Also, it is desirable to incorporate the acidic substance in such a way that the pH of the injectable solution of this invention may be adjusted finally to 7 to 11.

Employing the said solvent having the above-mentioned acidic substance admixed can permit the lyophilized material containing Compound (I) to be dissolved quickly, and it is preferable to dissolve or dilute the material on the occasion of use.

As the injectable solution of this invention, there may be employed a liquid composition having Compound (I) in conjunction with a strongly basic substance like the previously mentioned ones dissolved in the above-described solvent, which is to be diluted with a solvent being admixed with the above-mentioned acidic substance on the occasion of use to adjust its pH to the physiologically allowable range (ca. 7 to 11).

The injectable solutions thus prepared desirably have the concentration of Compound (I) of 0.1 to 20 mg/ml, particularly 2 to 10 mg/ml.

In addition, it is preferable to incorporate the injectable solution according to the present invention with additives, including buffer solutions for the stabilization of its pH, such as arginine, N-methylglucamine, glycine, sodium dihydrogenphosphate, disodium hydrogenphosphate, isotonizing agents for the adjustment of its osmotic pressure, such as sodium chloride, stabilizers, such as sodium hydrogensufite, pain-relieving agents, such as glucose, sorbitol, mannitol, benzyl alcohol, mepivacaine hydrochloride and xylocaine hydrochloride, and preservatives, such as methyl p-oxybenzoate, propyl p-oxybenzoate, thymelosal and chlorobutanol, as the case may be. These substances can added usually in an amount of 0.2 to 10 mg, preferably 0.5 to 5 mg, per mg of Compound (I).

In order to enhance the solubility of Compound (I), also there can be incorporated sodium chloride, magnesium chloride and potassium chloride. The amount of these salts in the formulation is usually 1 to 30 mg, preferably 3 to 15 mg, per mg of Compound (I).

The injectable solution of this invention is preferably prepared normally by means of the sterile preparation method known per se.

It is preferable to administer usually the said injectable solution intravenously, and its dosage amount is desirably selected in such a way that it may be 5 to 100 mg of Compound (I) daily for male adults, preferably 10 to 50 mg.

In the injectable solution of this invention, the use of at least one of ethanol, propylene glycol and polyethylene glycol as a solvent renders Compound (I) soluble in water and can contribute to the provision of desired stability to Compound (I). Consequently, it becomes possible to have Compound (I) demonstrate its excellent anti-ulcer activity in an adequate manner.

Below described are the examples to illustrate this invention specifically, but these are not to be understood to limit the scope of this invention.

EXAMPLE 1

Compound (I-1) was dissolved in ethanol and propylene glycol to the concentration of 2 mg/ml, respectively, and the resulting solutions were sterile filtered and filled in 5-ml portions into ampoules of a 5-ml capacity, followed by sealing.

The test specimens as filled into the ampoules were investigated for appearance, clarity and content of Compound (I) immediately after preparation and after storage at 25° C. for 24 hours, with the results being shown in Table 1. The test specimens prepared by dissolution in ethanol and propylene glycol were observed to produce a slight change in appearance after storage at 25° C. for 24 hours, but the changes were judged to be so slight that they might in no way influence the injectable solution. The test specimens were found to be stable in terms of content of the active ingredient.

TABLE 1

Stability of Compound (I-1) in the solution state:

| Composition of test specimen (in 1 ml) | Item of investigation | After preparation | After storage at 25° C./24 hrs. |
|---|---|---|---|
| Compound (I-1): 2 mg | Appearance | Colorless | Yellowish |
| Ethanol: 1 ml | Clarity | Clear | Clear |
| | Content* | 100.0% | 99.2% |
| Compound (I-1): 2 mg | Appearance | Colorless | Light red-purple |
| Propylene glycol: 1 ml | Clarity | Clear | Clear |
| | Content* | 100.0% | 103.0% |

Note. *As measured by use of high-performance liquid chromatography (HPLC), whereby the content determined immediately after preparation was taken as 100.0% (the same method was employed for measurement in examples to be described in the following).
chromatographic conditions of HPLC:
Carrier; Nucleosil 5 $C_{18}$ (supplied by Gas-Chro Kogyo K.K. of Japan) 4.0 mm × 150 mm
Solvent; Methanol:water:triethylamine (60:40:1, pH 7)
Detection method; UV spectrophotometry at 285 nm

EXAMPLE 2

Ethanol, polyethylene glycol 400, propylene glycol and water were mixed at the composition ratios as shown in Table 2 illustrated below, and 2 mg of Compound (I-1) was dissolved in 1 ml each of the resulting solvents, respectively, followed by adjustment to pH 9.0 with 5N-aqueous sodium hydroxide solution. As a control, there were prepared a suspension of 2 mg of Compound (I-1) in 1 ml of water being adjusted to pH 9.0 with 5N-aqueous sodium hydroxide solution and an aqueous solution of 2 mg of Compound (I-1) in 1 ml of 0.01N aqueous sodium hydroxide solution. These solutions were sterile-filtered by the conventional method and were filled in 5-ml portions into ampoules of a 5-ml capacity, respectively, followed by sealing.(A control of the suspension was not subjected to sterile-filtration). The test specimens as filled into ampoules were investigated for each item of appearance, pH and content immediately after preparation and after storage at 25° C. for 24 hours, with the results being shown in Table 2.

As may be evident, from Table 2, all of the test specimens, except the controls, were observed to produce a slight change in appearance after storage at 25° C. for 24 hours, but the changes were judged to be so slight that they might in no way influence the injectable solution. In addition, the test specimens were found to show slight change in content. The control specimens, when adjusted to the same pH value as other test specimens, failed to allow adequate dissolution of Compound (I-1), and were needed to be adjusted to a pH of not less than 11 in order to secure dissolution.

TABLE 2

Stability of Compound (I-1) in the solution state

| Composition of test specimen (in 1 ml) | Item investigation | After preparation | After storage at 25° C./24 hrs. |
|---|---|---|---|
| Compound (I-1): 2 mg | Appearance | Colorless | Slightly to light green-yellow |
| PEG-400*: 0.05 ml | pH | 9.0 | — |
| Ethanol: 0.35 ml | Content | 100.0% | 98.0% |
| Water: 0.6 ml | | | |
| Compound (I-1): 2 mg | Appearance | Colorless | Slightly to light green to yellow |
| PEG-400: 0.05 ml | pH | 9.0 | — |
| Propylene glycol: 0.35 ml | Content | 100.0% | 94.4% |
| Water: 0.6 ml | | | |
| Compound (I-1): 2 mg | Appearance | Colorless | Slightly to light green-yellow |
| PEG-400: 0.4 ml | pH | 9.0 | — |

TABLE 2-continued

Stability of Compound (I-1) in the solution state

| Composition of test specimen (in 1 ml) | Item investigation | After preparation | After storage at 25° C./24 hrs. |
|---|---|---|---|
| Water: 0.6 ml | Content | 100.0% | 91.8% |
| Compound (I-1): 2 mg | Appearance | Colorless | Slightly to light red-purple |
| Ethanol: 0.5 ml | pH | 9.0 | — |
| Propylene glycol: 0.5 ml | Content | 100.0% | 98.0% |
| Compound (I-1): 2 mg | appearance | White suspension | Slightly to light grey suspension |
| Water: 1 ml | pH | 9.1 | — |
| | Content | — | — |
| Compound (I-1): 2 mg | Appearance | Colorless | Colorless |
| 0.01 N aq. sodium hydroxide sol'n.: 1 ml | pH | 11.4 | — |
| | Content | 100.0% | 92.5% |

Note, *Polyethylene glycol having an average molecular weight of 400.

EXAMPLE 3

Ethanol, polyethylene glycol 400, propylene glycol and water were mixed at the composition ratios as shown in Table 3 illustrated below, and 5-mg of Compound (I-1) was dissolved in 1 ml each of the resulting solvents, respectively, followed by adjustment to pH 9.0 with 5N-aqueous sodium hydroxide solution. As a control, there were prepared a suspension of 5 mg of Compound (I-1) in 1 ml of water being adjusted to pH 9.0 with 5N-aqueous sodium hydroxide solution and an aqueous solution of 5 mg of Compound (I-1) in 1 ml of 0.02N aqueous sodium hydroxide solution. These solutions were sterile-filtered by the conventional method and were filled in 5-ml portions into ampoules of a 5-ml capacity, respectively, followed by sealing. (A control of the suspension was not subjected to sterile-filtration).

These test specimens as filled into ampoules were investigated for each item of appearance, pH and clarity immediately after preparation and after storage at 25° C. 24 hours, with the results being shown in Table 3.

As may be evident from Table 3, all of the test specimens, except the controls, were observed to produce a slight change in appearance after storage at 25° C. for 24 hours, but the changes were judged to be so slight that they might in no way influence the injectable solution. In addition, they were observed to shown no change in clarity. The control specimens, when adjusted to the same pH value as other test specimens, failed to allow adequate dissolution of Compound (I-1), and were needed to be adjusted to a pH of not less than 11 in order to secure dissolution.

TABLE 3

Stability of Compound (I-1) in the solution state

| Composition of test specimen (in 1 ml) | Item investigation | After preparation | After storage at 25° C./24 hrs. |
|---|---|---|---|
| Compound (I-1): 5 mg | Appearance | Colorless | Slightly to light green-yellow |
| Ethanol: 0.6 ml | pH | 9.0 | — |
| water: | Clarity | Clear | Clear |
| Compound (I-1): 5 mg | Appearance | Colorless | Slightly to light green-yellow |
| PEG-400*: 0.4 ml | pH | 9.0 | — |
| Water: 0.6 ml | Clarity | Clear | Clear |
| Compound (I-1): 5 mg | Appearance | Colorless | Slightly to light green-yellow |
| Ethanol: 0.3 ml | pH | 9.0 | — |
| Propylene glycol: | Clarity | Clear | Clear |

TABLE 3-continued

Stability of Compound (I-1) in the solution state

| Composition of test specimen (in 1 ml) | Item investigation | After preparation | After storage at 25° C./24 hrs. |
|---|---|---|---|
| 0.3 ml Water: 0.4 ml Compound (I-1): 5 mg PEG-400: 0.3 ml Ethanol: 0.3 ml Water: 0.4 ml | Appearance pH Clarity | Colorless 9.0 Clear | Slightly to light green-yellow — Clear |
| Compound (I-1): 5 mg Water: 1 ml | Appearance pH Clarity | White suspension 8.9 — | Slightly to light grey suspension — — |
| Compound (I-1): 5 mg 0.02 N aq. sodium hydroxide sol'n.: 1 ml | Appearance pH Clarity | Colorless 11.6 Clear | Colorless — Clear |

EXAMPLE 4

TABLE 5

Composition of the aqueous solution to be filled into vials (in 1 ml)

| Ingredient | No. 1 | No. 2 | No. 3 |
|---|---|---|---|
| Compound (I-1) | 15 mg | 15 mg | 15 mg |
| Mannitol | 15 mg | 50 mg | 15 mg |
| Sodium hydroxide | 2.4 mg | 2.4 mg | 4.8 mg |
| Distilled water | Suitable volume to make up to the total of 1 ml. | | |

TABLE 6

Composition of the lyophilized vials (per vial)

| Ingredient | V1 | V2 | V3 |
|---|---|---|---|
| Compound (I-1) | 30 mg | 30 mg | 30 mg |
| Mannitol | 30 mg | 100 mg | 30 mg |
| Sodium hydroxide | 4.8 mg | 4.8 mg | 9.6 mg |

TABLE 7

Compositions after being dissolved (per 10 ml)

| Ingredient | S1 | S2 | S3 | S4 | S5 |
|---|---|---|---|---|---|
| PEG-400 | 3000 mg | 3000 mg | 3000 mg | 3000 mg | 3000 mg |
| Sodium chloride | 90 mg | 90 mg | 90 mg | 90 mg | 90 mg |
| N-methyl-glucamine | 10 mg | 40 mg | 40 mg | — | — |
| NaH₂PO₄.-2H₂O | — | — | — | 13 mg | 50 mg |
| Hydrochloric acid | 1.1 mg | 7.7 mg | 8.4 mg | — | — |
| Sodium hydroxide | — | — | — | 2.8 mg | 11 mg |
| pH | 9.0 | 3.1 | 8.5 | 8.5 | 7.0 |

A 1000 mg quantity of Compound (I-1) was dispersed in distilled water for injection, and 3 ml of 1N-aqueous sodium hydroxide solution was added to dissolve the Compound (I-1), followed by addition of water to make up the total of 50 ml and sterile filtration by the conventional method. The resulting filtrate was filled in 1 ml portions into vials of a 12 cm³ capacity, followed by lyophilization by means of the conventional technique. The lyophilized powder as contained in vials was dissolved in in Solvent A (which was composed of 50 mg of N-methylglucamine, 0.27 ml of 1N-hydrochloric acid and 2 ml of propylene glycol being admixed with ethanol to make up the total of 4 ml), Solvent B (which was composed of 50 mg of N-methylglucamine, 0.27 ml of 1N-hydrochloric acid, 1.2 ml of polyethylene glycol 400 and 1.2 ml of ethanol being admixed with distilled water for injection to make up the total of 4 ml), Solvent C (which was composed of 50 mg of N-methylglucamine, 0.27 ml of 1N-hydrochloric acid, 1.2 ml of ethanol and 1.2 ml of propylene glycol being admixed with distilled water for injection to make up the total of 4 ml and Solvent D (which was composed of 50 mg of N-methylglucamine, 0.27 ml of 1N-hydrochloric acid and 2.5 ml of polyethylene glycol 400 bing admixed with distilled water for injection to make up the total of 4 ml), respectively, to perform inspection for their solubilities as well as to conduct investigation into appearance, clarity and contents immediately after dissolution and after storage at 25° C. for 24 hours.

The results are shown in Table 4. The lyophilized powder showed excellent solubilities in all of these solvents, and were able to be dissolved quickly. In addition to this, the resulting solutions was observed to produce slight changes in appearance immediately after dissolution and after storage for 24 hours, but the changes were found to be so slight that they might in no way influence the injectable solution. The solutions were found to show no change in the clarity while being observed to decrease slightly in content of Compound (I-1).

TABLE 4

Stability of lyophilized Compound (I-1) after being dissolved in vials:

| Item | Solvent A | Solvent B | Solvent C | Solvent D |
|---|---|---|---|---|
| Solubility | Good | Good | Good | Good |
| pH after dissolution | 8.7 | 9.0 | 9.0 | 9.0 |
| After dissolution: | | | | |
| Appearance | Colorless | Colorless | Colorless | Colorless |
| Clarity | Clear | Clear | Clear | Clear |
| Content | 100% | 100% | 100% | 100% |
| After storage at 25° C. for 24 hrs.: | | | | |
| Appearance | Slightly to lightly green-yellow | | | |
| Clarity | Clear | Clear | Clear | Clear |
| Content | 97.0% | 96.5% | 96.7% | 96.1% |

EXAMPLE 5

There were prepared 100 ml each of three kinds of aqueous solutions containing Compound(I-1), mannitol and sodium hydroxide at the individually different compositions per ml as shown in Table 5. The resulting aqueous solutions were sterile-filtered by the conventional method, and the filtrates were filled in 2 ml portions into vials of a 18 cm³ capacity, respectively, followed by lyophilization by the conventional technique to give three kinds of lyophilized vials (V1, V2 and V3) having the compositions as shown in Table 6.

Then, there were prepared 500 ml each of five kinds of aqueous solutions containing PEG-400, sodium chloride, N-methylglucamine, sodium bihydrogenphosphate, hydrochloric acid and sodium hydroxide at the individually different compositions per each 10 ml as shown in Table 7. The aqueous solutions were sterile-filtered by the conventional method, and the resulting filtrates were filled in 10 ml portions into ampoules of a 10 ml capacity, respectively. The ampoules were sealed and sterilized by high-pressure steam at 115° C. for 30 minutes to give five kinds of the solutions for dissolution (S1, S2, S3, S4 and S5) having the individual formulations as shown in Table 7.

Following the combinations as described in Table 8, then, the lyophilized vials were dissolved again in the solutions for dissolution, and the resulting drug solutions were investigated for pH and state of clarity immediately after preparation and after storage at 25° C. for 24 hours. As may be evident from the results shown in Table 8, the drug solutions resulting from any of the combinations were found to be stable in pH and good in clarity, whereby the lyophilized vials after being dissolved by any of the combinations exhibited good solubility.

TABLE 5

Composition of the aqueous solution to be filled into vials (in 1 ml)

| Ingredient | No. 1 | No. 2 | No. 3 |
|---|---|---|---|
| Compound (I-1) | 15 mg | 15 mg | 15 mg |
| Mannitol | 15 mg | 50 mg | 15 mg |
| Sodium hydroxide | 2.4 mg | 2.4 mg | 4.8 mg |
| Distilled water | Suitable volume to make up to the total of 1 ml. | | |

TABLE 8

Stability after dissolution of lyophilized vials containing Compound (I-1)

| Combination | | Stability | | | |
|---|---|---|---|---|---|
| | | Immediately after preparation | | After storage at 25° C. for 24 hrs. | |
| Vial | Solution for diss'n | pH | Clarity | pH | Clarity |
| V1 | S1 | 9.8 | Clear | 9.8 | Clear |
| V2 | S1 | 9.9 | Clear | 9.8 | Clear |
| V3 | S2 | 10.1 | Clear | 9.9 | Clear |
| V1 | S4 | 9.9 | Clear | 10.0 | Clear |
| V2 | S4 | 10.2 | Clear | 10.0 | Clear |
| V3 | S5 | 10.0 | Clear | 9.9 | Clear |

EXAMPLE 6

There were prepared 100 ml each of three kinds of aqueous solutions containing Compound (I-1), mannitol, N-methylglucamine and sodium hydroxide at individually different compositions per ml as shown in Table 9. The aqueous solutions were sterile-filtered in a conventional manner, and the filtrate were filled in 2 ml portions into vials of 18 cm³ capacity, respectively, followed by lyophilization in a conventional manner to give three kinds of lyophilized vials (No. V4, V5 and V6) having the compositions as shown in Table 10.

Subsequently, there were prepared 500 ml each of three kinds of aqueous solutions containing PEG-400 and sodium hydroxide at individually different compositions per each 10 ml as shown in Table 11. The aqueous solution were sterile-filtered in a conventional manner, and the resulting filtrate were filled in 10 ml portions into ampoules, respectively. The ampoules were sealed and sterilized with high-pressure steam at 115° C. for 30 minutes to give three kinds of solutions for dissolution ((No. S6, S7 and S8) as shown in Table 11.

Then, following the combinations as shown in Table 12, the contents of the lyophilized vials were dissolved again in the solutions for dissolution, and the resulting drug solutions were investigated for pH and clarity immediately after preparation and after storage at 25° C. for 24 hours.

As evident from the results shown in Table 12, the drug solutions obtained from any of the combinations were found to be stable in pH and good in clarity. In addition, the contents of the lyophilized vials exhibited good solubility to any one of the combination.

TABLE 9

Compositions of the aqueous solution to be filled into vials (in 1 ml)

| Ingredient | No. 1 | No. 2 | No. 3 |
|---|---|---|---|
| Compound (I-1) | 15 ml | 15 mg | 15 mg |
| Mannitol | 30 mg | 30 mg | 30 mg |
| N-methylglucamine | 10 mg | 5 mg | 2.5 mg |
| Sodium hydroxide | 2.4 mg | 2.4 mg | 2.4 mg |
| Distilled water for injection | making 1 ml in total | making 1 ml in total | making 1 ml in total |

TABLE 10

Compositions of lyophilized ampoules (in one vial)

| Ingredient | No. V4 | V5 | V6 |
|---|---|---|---|
| Compound (I-1) | 30 mg | 30 mg | 30 mg |
| Mannitol | 60 mg | 60 mg | 60 mg |
| N-methylglucamine | 20mg | 10 mg | 5 mg |
| Sodium hydroxide | 4.8 mg | 4.8 mg | 4.8 mg |

TABLE 11

Compositions of solutions for dissolution (in 10 ml)

| Ingredient | No. S6 | S7 | S8 |
|---|---|---|---|
| PEG-400 | 3000 mg | 3000 mg | 3000 mg |
| NaH₂PO₄.2H₂O | 7.8 mg | 6.2 mg | 5.5 mg |
| Sodium hydroxide | proper amount | proper amount | proper amount |
| pH | 6.7 | 6.7 | 6.7 |

TABLE 12

Stability of Compound (I-1) contained in lyophilized vials after dissolution

| Combination | | Stability | | | |
|---|---|---|---|---|---|
| | | Immediately after dissolution | | After 24 hours at 25° C. | |
| Vial | Solution for dissolution | pH | Clarity | pH | Clarity |
| V4 | S6 | 10.4 | Clear | 10.4 | Clear |
| V5 | S7 | 10.4 | Clear | 10.3 | Clear |
| V6 | S8 | 10.3 | Clear | 10.2 | Clear |

We claim:

1. An injectable solution made by the process comprising the steps of:
(a) freeze drying an aqueous solution having a pH not less than 11 and comprising a compound represented by the formula:

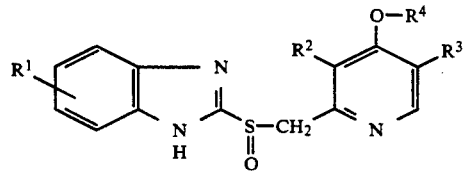

wherein R¹ represents hydrogen, methoxy or trifluoromethyl group, R² and R³, being the same or different from each other, represent hydrogen or methyl group, and R⁴ represents a fluorinated $C_2$ to $C_5$ lower alkyl group, and N-methylglucamine; and (b) mixing the freeze-dried material with polyethylene glycol 400 and an acidic substance in water to obtain and injectable solution having a pH of 7 to 11.

2. An injectable solution according to claim 1, of pH 7 to 11 which comprises a solution wherein a freeze-dried material of an alkaline aqueous solution containing N-methylglucamine and a compound represented by formula;

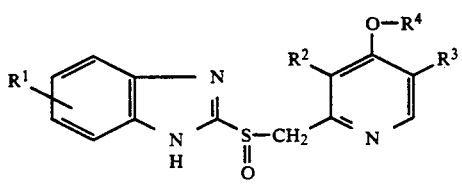

wherein $R^1$ represents hydrogen, methoxy or trifluoromethyl group, $R^2$ and $R^3$, being the same as or different from each other, represent hydrogen or methyl group; and $R^4$ represents a fluorinated $C_2$ to $C_5$ lower alkyl group, said alkaline aqueous solution being not less than pH 11, has been dissolved with a mixed solution of (a) an acidic substance and (b) polyethylene glycol 400.

3. An injectable solution according to claim 1, wherein said freeze-dried material is a freeze-dried material of said alkaline aqueous solution containing a saccharide besides said compound.

4. An injectable solution according to claim 1, wherein said saccharide is mannitol.

5. An injectable solution according to claim 1, wherein said acidic substance is hydrochloric acid or sodium dihydrogenphosphate.

6. An injectable solution according to claim 1, wherein said mixed solution additionally contains sodium chloride.

7. An injectable solution according to claim 1, wherein said mixed solution contains N-methylglucamine and sodium chloride.

8. An injectable solution according to claim 1, wherein said acidic substance is hydrochloric acid or sodium dihydrogenphosphate.

9. An injectable solution made by the process comprising the steps of:

(a) freeze drying an aqueous solution having a pH not less than 11 and comprising a compound represented by the formula:

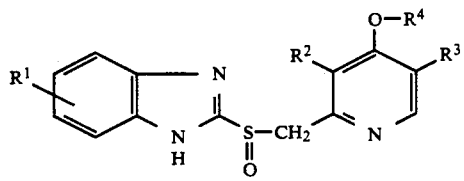

wherein $R^1$ represents hydrogen, methoxy or trifluoromethyl group, $R^2$ and $R^3$, being the same or different from each other, represent hydrogen or methyl group, and $R^4$ represents a fluorinated $C_2$ to $C_5$ lower alkyl group; and (b) mixing the freeze-dried material with polyethylene glycol 400, an acidic substance and N-methylglucamine in water to obtain an injectable solution having a pH of 7 to 11.

10. An injectable solution according to claim 9, of pH 7 to 11 which comprises a solution wherein a freeze-dried material of an alkaline aqueous solution containing N-methylglucamine and a compound represented by formula;

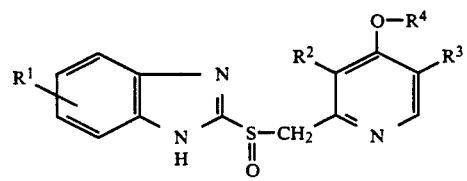

wherein $R^1$ represents hydrogen, methoxy or trifluoromethyl group, $R^2$ and $R^3$, being the same as or different from each other, represent hydrogen or methyl group; and $R^4$ represents a fluorinated $C_2$ to $C_5$ lower alkyl group, said alkaline aqueous solution being not less than pH 11, has been dissolved with a mixed solution of (a) an acidic substance and (b) polyethylene glycol 400.

11. An injectable solution according to claim 9, wherein said freeze-dried material is a freeze-dried material of said alkaline aqueous solution containing a saccharide besides said compound.

12. An injectable solution according to claim 9, wherein said saccharide is mannitol.

13. An injectable solution according to claim 9, wherein said acidic substance is hydrochloric acid or sodium dihydrogenphosphate.

14. An injectable solution according to claim 9, wherein said mixed solution additionally contains sodium chloride.

15. An injectable solution according to claim 9, wherein said mixed solution contains N-methylglucamine and sodium chloride.

16. An injectable solution according to claim 9, wherein said acidic substance is hydrochloric acid or sodium dihydrogenphosphate.

* * * * *